US00PP08274P

United States Patent [19]

Jacobsen

[11] Patent Number: Plant 8,274

[45] Date of Patent: Jun. 22, 1993

[54] POINSETTIA PLANT 'PEGIRL'

[75] Inventor: Peter Jacobsen, Skibby, Denmark

[73] Assignee: Paul Ecke Ranch, Inc., Encinitas, Calif.

[21] Appl. No.: 727,611

[22] Filed: Jul. 10, 1991

[51] Int. Cl.[5] ..... A01H 5/00

[52] U.S. Cl. ..... Plt./86.3

[58] Field of Search ..... Plt./86.4, 86.3

[56] References Cited

U.S. PATENT DOCUMENTS

P.P. 5,492 6/1985 Gutbeir ..... Plt. 86.4

P.P. 7,310 8/1990 Neuhaus ..... Plt. 86.3

*Primary Examiner*—James R. Feyrer

*Attorney, Agent, or Firm*—Arnold, White & Durkee

[57] ABSTRACT

The present invention describes a Poinsettia cultivar, designated 'Pegirl', that is vigorous and self-branching, having a medium height and large pink flower bracts. 'Pegirl' originated as an induced mutation of 'Angelika' (U.S. Plant Pat. No. 5,492). The bracts of 'Pegirl' are lighter pink than 'Dorothee' (U.S. Plant Pat. No. 7,310), the cultivar it most closely resembles. 'Pegirl' retains the unique characteristics and growth habits of the Angelika family of poinsettia plants, including prolific multiple branching, full bracts and tight, full cyathia clusters.

1 Drawing Sheet

BACKGROUND OF THE INVENTION

'Pegirl' is a vigorous, strong growing Poinsettia of medium height and large pink flower bracts. It has self-branching traits which make it desirable for branched plant production. 'Pegirl' blooms relatively early and the blooming time is very uniform among individual clones. The bract presentation is slightly umbrella shaped, but the plant does not exhibit epinasty after sleeving and shipping.

This new Poinsettia cultivar originated as an induced mutation of 'Angelika' (U.S. Plant Pat. No. 5,492) at greenhouses in Skibby, Denmark. It most closely resembles the cultivar 'Dorothee', U.S. Plant Pat. No. 7,310, but differs in that bract color of 'Pegirl' is a lighter pink. 'Pegirl' was induced from the variety 'Angelika' using 2500 RAD of gamma rays, and was selected from about 200 mutants so produced.

After selection, vegetative reproduction of this plant was accomplished by stem cuttings for further testing purposes. Clones were subjected to successive generations of vegetative propagation which demonstrated that bract coloration and other distinctive characteristics held true from generation to generation.

DESCRIPTION OF THE PHOTOGRAPHS

Poinsettia cultivar 'Pegirl' is illustrated in the accompanying color photographs. The upper photo is a side view of a typical pinched plant with several flowering stems. The lower photo is a top view of the same plant, showing flower and bract formation.

DESCRIPTION OF THE PLANT

The following is a detailed description of this new Poinsettia as observed in greenhouses in Encinitas, Calif., during December, 1990. Some observations are compared to the cultivar 'Dorothee', U.S. Plant Pat. No. 7,310, grown at the same time, in the same greenhouse and under the same cultural conditions. Color designations are compared to the 1986 edition of R.H.S. Colour Chart, first published in 1966 by The Royal Horticultural Society, London, England.

THE PLANT

Origin: An induced mutation of 'Angelika' (U.S. Plant Pat. No. 5,492).

Classification:

*Botanic.*—*Euphorbia pulcherrima* Willd.

*Common name.*—Poinsettia.

*Cultivar name.*—'Pegirl'.

Form: Shrub.

Height: Medium.

Growth habit: As a single stemmed plant, upright and vigorous. In full flower, the stem is terminated by a large inflorescence, with smaller flowering side shoots lower on the stem. The average overall height of single stemmed plants was 48 cm.

Branching: Branching can be enhanced by removal of the stem tip. Then, several flowering branches with equal vigor will develop on a single plant.

Growth rate: Very fast. Rooing of stem cuttings occurs in 12–18 days under intermittent mist. The plant will flower in about nine weeks under continuous long night conditions and night temperatures of about 16–18 degrees C.

Foliage: The foliage is clean and uniformly green from bottom to top of the plant. The leaves are of medium size, leaf blades typically being 14–16 cm. long and 9–11 cm. wide with leaf petioles 6–7 cm. long. In contrast to 'Angelika' which has red leaf petioles, 'Pegirl' has green leaf petioles.

*Leaf shape.*—Typical leaves are ovate with acute to obtuse bases and acuminate tips. Leaf margins are mostly entire to slightly lobed with usually one lobe on either side of the leaf blade.

*Leaf surface.*—Upper surface is glabrous and smooth. The under surface is slightly pubescent.

*Leaf color.*—Upper side — Between RHS 147A and RHS 147B, lighter green than 'Dorothee' which is darker than RHS 147A. Under side — Between RHS 147B and RHS 147C.

*Retention.*—The foliage retention is good even under low light intensities in the consumer's home.

Bracts: Generally there are 21–24 bracts of various sizes subtending the cyathia as compared to the parent 'Angelika' which typically exhibits about 17 to 12 bracts in overlapping arrangement with a tight center. The primary bracts have blades typically 15–17 cm. long and 11–12 cm. wide with petioles 2–3 cm. long.

Bract shape.—Bracts are mostly ovate to elliptic for the smaller bracts, with acute bases and acuminate tips. Bract margins are mostely entire, but primary bracts may have slight lobing on either side of the bracts.

*Bract surface.*—The bract surface is slightly rugose.

*Bract color.*—Upper side — Pink, between RHS 51B and RHS 51C. The bracts are lighter pink than 'Dorothee' which is nearer RHS 51B. The bract color is significantly different from that of 'Angelika', which typically ranges from about 45A to about 46B RHS. Under side — Light pink, between RHS 51C and RHS 51D.

Cyathia: Generally, 18–21 cyathia (flowers) develop when the plant is in "full bloom". Each cyathium is 7–8 mm long and 6–7 mm wide, primarily green in color but creamy at the distal end. One or two yellow nectar cups protrude from the side of each cyathium. The flower pedicel is green and 7–8 mm in length. The stamens protruding from the cyathia are red. There are typically 10–12 anthers ripening at any one time. The pollen produced is yellow and copious. Flowers are self-incompatible and thus no viable seed is formed without cross-pollination.

Retention: The post production retention of the cyathia is good.

What is claimed is:

1. A new and distinct Poinsettia cultivar, substantially as herein shown and described, distinguished by its vigorous and self-branching growth habits, medium height and large pink flower bracts.

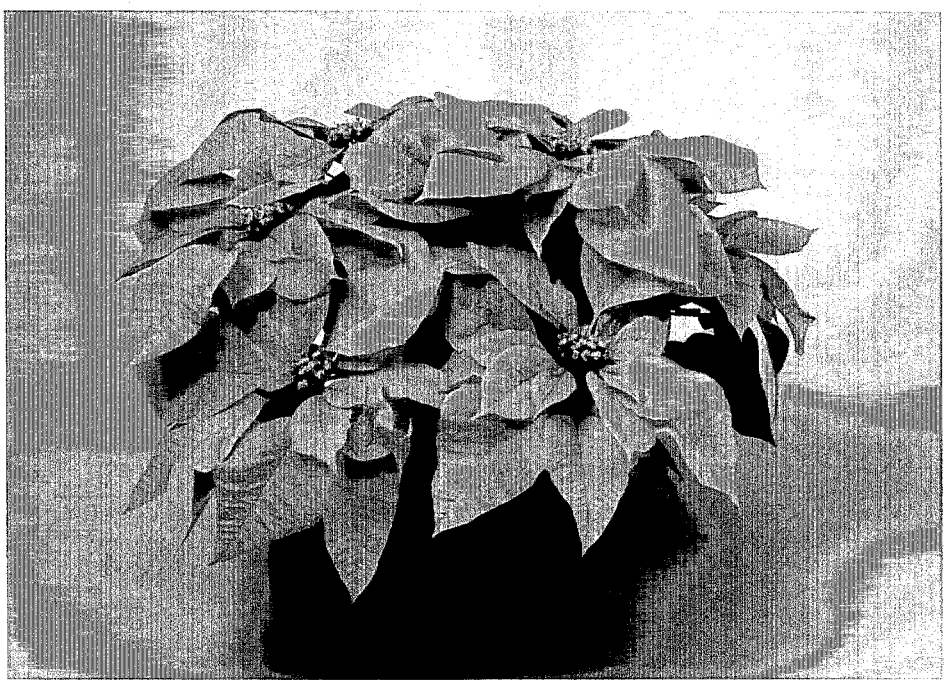
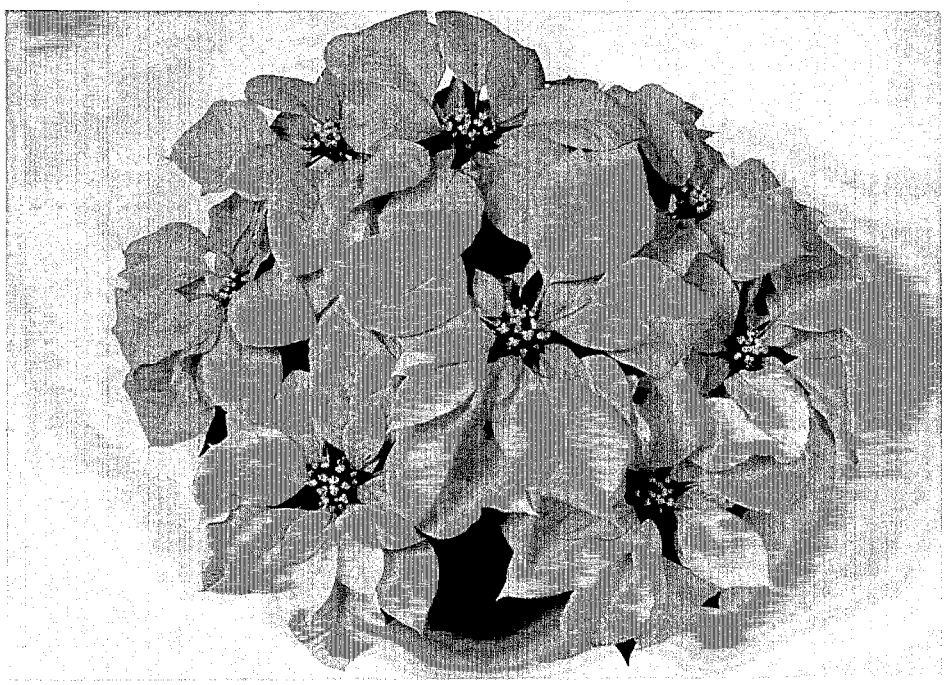

* * * * *